United States Patent
Righetti et al.

(10) Patent No.: US 7,954,379 B2
(45) Date of Patent: Jun. 7, 2011

(54) METHODS FOR DETERMINING DISPLACEMENT OR STRAIN OF A TARGET BODY

(75) Inventors: Raffaella Righetti, Houston, TX (US); Jonathan Ophir, Austin, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 95 days.

(21) Appl. No.: 12/501,419

(22) Filed: Jul. 11, 2009

(65) Prior Publication Data

US 2010/0010353 A1 Jan. 14, 2010

Related U.S. Application Data

(62) Division of application No. 11/436,129, filed on May 17, 2006, now Pat. No. 7,779,692.

(51) Int. Cl.
  G01N 29/50 (2006.01)
  G01N 29/04 (2006.01)
  A61B 8/08 (2006.01)
(52) U.S. Cl. .......................................... 73/602; 73/614
(58) Field of Classification Search .............. 73/602, 73/614; 600/437, 449; 702/42, 56, 150, 702/159, FOR. 126, FOR. 146
See application file for complete search history.

(56) References Cited

U.S. PATENT DOCUMENTS

| | | | |
|---|---|---|---|
| 4,853,904 A * | 8/1989 | Pesque | 367/89 |
| 5,107,837 A * | 4/1992 | Ophir et al. | 600/437 |
| 5,293,870 A | 3/1994 | Ophir et al. | |
| 5,474,070 A | 12/1995 | Ophir et al. | |
| 6,270,459 B1 | 8/2001 | Konofagou et al. | |
| 6,364,838 B1 * | 4/2002 | Freiburger et al. | 600/455 |
| 6,508,768 B1 * | 1/2003 | Hall et al. | 600/443 |
| 6,687,625 B2 | 2/2004 | Srinivasan et al. | |
| 7,850,611 B2 * | 12/2010 | Davies et al. | 600/437 X |
| 2004/0034304 A1 * | 2/2004 | Sumi | 600/439 |
| 2006/0074311 A1 * | 4/2006 | Sakai et al. | 600/437 |
| 2006/0285731 A1 * | 12/2006 | Jiang et al. | 382/128 |
| 2009/0301204 A1 * | 12/2009 | Righetti et al. | 73/627 |
| 2010/0152579 A1 * | 6/2010 | Lin et al. | 600/437 |
| 2010/0180684 A1 * | 7/2010 | Righetti et al. | 73/620 |
| 2010/0204955 A1 * | 8/2010 | Roche et al. | 702/159 |
| 2010/0251820 A1 * | 10/2010 | Righetti et al. | 73/602 |

OTHER PUBLICATIONS

Konofagou EE, Harrigan TP, Ophir J, Krouskop TA., Poroelastography: imaging the poroelastic roperties of tissues, Ultrasound Med Biol 27, No. 10, 1387-1397 (2001).

Mow VC, Holmes MH, Lai WM., Fluid transport and mechanical properties of articular cartilage: a review, J Biomechanics, 17(5), 377-394 (1984).

Mridha M, Ödman S., Noninvasive method for assessment of subcutaneous edema, Med and Biol. Eng. and Comp., 24, 393-398 Jul. 1986.

Netti PA, Berk DA, Swartz MA, Grodzinsky AJ, Jain RK., Role of extracellular matrix assembly in interstitial transport in solid tumors, Cancer Research, 60, 2497-2503 May 2000.

(Continued)

*Primary Examiner* — Thomas P Noland
(74) *Attorney, Agent, or Firm* — Browning Bushman P.C.

(57) ABSTRACT

The invention is directed toward a new method for estimating and imaging the spatial and temporal mechanical behavior of materials in responses to a mechanical stimulus. This method is designed to work in inherently noisy applications, such as the imaging of the time-dependent mechanical behavior of biological tissues in vivo and using a preferred hand-held configuration of scanning.

28 Claims, 9 Drawing Sheets

OTHER PUBLICATIONS

Reddy N, Cochran G, Krouskop TA. Interstitial fluid flow as a factor in decubitus ulcer formation, J Biomechanics, 14 (12), 879-881 (1981).

Righetti R, Ophir J, Srinivasan S, Krouskop TA. The feasibility of using elastography for imaging the Poisson's ratio in porous media, Ultrasound Med. Biol., 30, No. 2, 215-228 (2004).

Righetti R, Ophir J, Krouskop TA. A method for generating permeability elastograms and Poisson's ratio time constant elastograms, Ultrasound Med. Biol., 31, No. 6, 803-816 (2005).

Righetti R, Ophir J, Garra BS, Chandrasekhar RM, Krouskop TA. A new method for generating poroelastograms in noisy environments. Ultrasonic Imaging. 27, 201-220 (2005).

Alam, S. K. and Ophir, J.: An adaptive strain estimator for elastography, IEEE Trans. UFFC, vol. 45(2), pp. 461-472, Mar. 1998.

Armstrong, C.G., Lai, W.M. and Mow, V.C. An analysis of the unconfined compression of articular cartilage, J. Biomech. Eng., vol. 106 165-173, May 1984.

Berry GP, Bamber JC, Armstrong CG, Miller NR, Barbone PE. Towrads an acoustic model-based poroelastic imaging method: I. Theoretical foundation. Ultrasound in Medicine and Biology. 32 (4): 547-567, 2006.

Biot, M.A. Mechanics of deformation and acoustic propagation in porous media, J. Applied Physics, vol. 33 1482-1498, Apr. 1962, No. 4.

Brace, A.R. and Guyton, A.C. Interstitial fluid pressure: capsule, free fluid, gel fluid and gel absorption pressure in subcutaneous tissue, Microvasc. Res., vol. 18 217-227, 1979.

Brennan MJ, DePompolo RW, Garden FH. Focused review: postmastectomy lymphedema. Arch. Phys. Med. Rehabil., 77: S74-S80, Mar. 1996.

Brown JM, Giaccia AJ. The unique physiology of solid tumors: Opportunities (and problems) for cancer therapy. Cancer Research 58 (7): 1408-1416, Apr. 1998.

Cespedes I, Ophir J, Ponnekanti, et al. Elastography—Elasticity Imaging using ultrasound with application to muscle and breast in vivo. Ultrasonic Imaging. 15(2): 73-88, 1993.

Céspedes, I., Ophir, J., and Alam, S. K.: The combined effect of signal decorrelation and random noise on the variance of time delay estimation. IEEE Trans. on Ultrason., Ferroelec., & Freq. Contr., vol. 44(1), pp. 220-225, Jan. 1997.

Doyley, MM, Srinivasan, S, Dimidenko, E, Soni, N, and Ophir, J: Enhancing the perfomance of model-based elastography by incorporating additional a priori information in the modulus image reconstruction process. Physics in Medicine and Biology, 50, pp. 1-19, 2005.

Fortin, M., Buschmann, M.D., Bertrand, M.J., Foster, F.S. and Ophir, J. Dynamic measurement of internal solid displacement in articular cartilage using ultrasound backscatter, J. Biomech., vol. 36(3) 443-447, 2003.

Garra B.S., Cespedes E.I., Ophir J., Spratt R.S., Zuubier R.A., Magnant C.M. and Pennanen M.F., Elastography of breast lesions: initial clinical results, Radiology 202, 79-86 Jan. 1997.

Gerber LH. A review of measures of Lymphedema. Cancer Supplement. 83(12): 2803-2804 Dec. 1998.

Hall TJ, Zhu Y, Spalding CS. In vivo real-time freehand palpation imaging. Ultrasound in Medicine & Biology, 29 (3), 427-435, 2003.

Jurvelin, J.S., Buschmann, M.D. and Hunziker, E.B. Optical and mechanical determination of Poisson's ratio of adult bovine humeral articular cartilage, J. Biomechanics, vol. 30(3) 235-241, 1997.

Kallel, F. and Ophir, J.: A least squares estimator for elastography. Ultrasonic Imaging, vol. 19 (3), pp. 195-208, 1997.

Konofagou, E. E., Varghese, T. and Ophir, J.: Spectral Estimators in Elastography. Ultrasonics, vol. 38, pp. 412-416, 2000.

Konofagou, E.E. and Ophir, J. A new elastographic method for estimation and imaging of lateral displacements, lateral strains, corrected axial strains and Poisson's ratios in tissues, Ultras. Med. Biol., vol. 24 1183-1199, 1998.

Konofagou, E.E., Harrigan, T. and Ophir, Shear Strain Estimation and Lesion Mobility Assessment in Elastography, J. Estimation of normal and shear strain components in elastography, Ultrasonics, vol. 38, No. 10, 400-404, 2000.

Pesavento A, Perrey C, Krueger M, et al. A time-efficient and accurate strain estimation concept for ultrasonic elastography using iterative phase zero estimation. IEEE Trans. Ultras. Ferroelec. Freq. Control. 46 (5): 1057-1067, Sep. 1999.

Konofagou, E.E., Varghese, T. and Ophir, J. Theoretical bounds on the estimation of transverse displacement, transverse strain and Poisson's ratio in elastography, Ultrason. Imaging, vol. 22(3) 153-177, 2000.

Kyriacou, S.K., Mohamed, A., Miller, K. and Neff, S. Brain Mechanics for neurosurgery: modeling issues, Biomechanics and Modeling in Mechanobiology, vol. 1 151-164, 2002.

Leipzig ND, Athanasiou KA. Unconfined creep compression of chondrocytes. J. Biomechanics. 38: 77-85, 2005.

Mow, V.C., Kuei, S.C., Lai, W.M. and Armstrong, C.G. Biphasic creep and stress relaxation of articular cartilage in compression: theory and experiments, J. Biomech. Eng., vol. 102 73-84, Feb. 1980.

Varghese, T., Konofagou, E. E., Ophir, J., Alam, S. K. and Bilgen, M.: Direct Strain Estimation in Elastography Using Spectral Cross-Correlation. Ultrasound in Medicine and Biology, vol. 26, No. 9, pp. 1525-1537, 2000.

Chandrasekhar R.M., Ophir J., Krouskop T.A., Ophir D., Elastographic Image Quality vs. Tissue Motion In Vivo, Ultrasound in Med. & Biol., vol. 32, No. 6, pp. 847-855, 2006.

Nightingale K, Soo MS, Nightingale R, et al. Acoustic radiation force impulse imaging: In vivo demonstration of clinical feasibility. Ultrasound in Medicine & Biology, 28 (2): 227-235, 2002.

Ophir, J., Alam, K., Garra, B., Kallel, F., Konofagou, E.E., Krouskop, T.A. and Varghese, T. Elastography: ultrasonic estimation and imaging of the elastic properties of tissues, Proc. Inst. Mech. Eng. [H], vol. 213(3) 203-233, 1999. Review.

Ophir, J., Céspedes, E.I., Ponnekanti, H., Yazdi, Y. and Li, X. Elastography: a quantitative method for imaging the elasticity of biological tissues, Ultrasonic Imaging, vol. 13 111-134, 1991.

Rice, J. R.; Cleary, M. P. Some basic stress diffusion solutions for fluid-saturated elastic porous media with compressible constituents. Reviews of geophysics and space physics 14(2):227-241; May 1976.

Shiina T, Nitta N, Ueno E, et al. Real time tissue elasticity imaging using the combined autocorrelation method. J Med Ultrasonics. 29: 119-128, 2002.

Sinha, S. and Sinha, U. Functional Magnetic Resonance of Human Breast Tumors: Diffusion and Perfusion Imaging, Annals of the New York Academy of Sciences, vol. 980 (1) 95-115, 2002.

Souchon R., Rouviere O., Gelet A., Detti V., Srinivasan S., Ophir J. and Chapelon J.Y., Visualisation of HIFU lesions using elastography of the human prostate in vivo preliminary results, Ultrasound Med. Biol. 29, 1007-1015 (2003).

Srinivasan, S. and Ophir, J.: A zero-crossing strain estimator in elastography. Ultrasound in Medicine and Biology, vol. 29, No. 2, pp. 227-238. 2003.

Srinivasan, S., Ophir, J. and Alam, S.K. Elastographic imaging using staggered strain estimates, Ultrasonic Imaging, vol. 24(4) 229-245, 2002.

Srinivasan, S., Righetti, R. and Ophir, J. Trade-offs between the axial resolution and the signal-to-noise ratio in elastography, Ultras. Med. Biol., vol. 29(6) 847-866, 2003.

Techavipoo U, Chen Q, Varghese T, et al. Noise reduction using spatial-angular compounding for elastography. IEEE Trans. Ultras. Ferroelec. Freq. Control. 51 (5): 510-520, May 2004.

Torzilli, P.A. and Mow, V.C. On the fundamental fluid transport mechanisms through normal and pathological articular cartilage during function I, J. Biomech., vol. 9 541-552, 1976a.

Torzilli, P.A. and Mow, V.C. On the fundamental fluid transport mechanisms through normal and pathological articular cartilage during function II, J. Biomech., vol. 9 587-606, 1976b.

Van Houten EEW, Doyley MM, Kennedy FE, et al. Initial in vivo experience with steady-state subzone-based MR elastography of the human breast. J. of magnetic resonance imaging 17 (1): 72-85, 2003.

Varghese, T. and Ophir, J. A theoretical framework for performance characterization of elastography: The Strain Filter, IEEE Trans. Ultras. Ferroel. Freq. Cont., vol. 44(1) 164-172, Jan. 1997.

Varghese, T., Bilgen, M. and Ophir, J.: Multiresolution Imaging in elastography. IEEE Trans. Ultrason. Ferroel. Freq. Cont., vol. 45 (1), pp. 65-75, Jan. 1998.

Viola F, Walker WF. Radiation force imaging of viscoelastic properties with reduced artifacts. IEEE Trans. Ultrason. Ferroelec. Freq. Control. 50(6): 736-742, in Jun. 2003.

Witte CL, Witte MH, Unger EC, Williams WH, Bernas MJ, McNeill GC, Stazzone AM. Advances in imaging of lymph flow disorders. Radiographics 20 (6): 1697-1719, Nov.-Dec. 2000.

Wu, J. Tofu as a tissue-mimicking material, Ultras. Med. Biol., 27 1297-1300, 2001, No. 9.

Jain, R.K., Haemodynamic and transport barriers to the treatment of Solid Tumours, Int. J. RAdiat. Biol., vol. 60, Nos. 1/2, 85-100, 1991.

Folkman, J., Angiogenesis, Annual Review of Medicine, vol. 57. pp. 1-18 and C1-C2, 2006.

Science Direct, List of Issues, vol. 32, www.sciencedirect.com; 2 pages, Ultrasound in Medicine & Biology, Aug. 2006.

* cited by examiner

METHODS FOR DETERMINING DISPLACEMENT OR STRAIN OF A TARGET BODY

PRIORITY INFORMATION

This application is a divisional application which claims priority from U.S. patent application Ser. No. 11/436,129, filed on May 17, 2006.

GOVERNMENT RIGHTS

This invention was made with United States Government support under Grant No. NIH/NIBIB P01 EB 02105, awarded by the National Institutes of Health and National Institute of Biomedical Imaging and Bioengineering. The United States Government has certain rights in the invention.

BACKGROUND OF THE INVENTION

1. Field of the Invention

The invention is directed toward new methods for estimating and imaging the spatial and temporal mechanical behavior of materials in response to a mechanical stimulus. These methods are designed to work in inherently noisy applications, such as the imaging of the time-dependent mechanical behavior of biological tissues in vivo and using a preferred hand-held configuration of scanning.

Embodiments of the invention overcome the limitation of current elastographic methods for imaging local strains and displacements in inherently noisy environments, which are primarily due to echo decorrelation problems generated by uncontrollable motion. Embodiments of the invention minimize the decorrelation noise between the ultrasonic frames used for the generation of the elastograms since the reference pre-compression frame is continuously moved in time and the inter-frame time interval is maintained sufficiently short during the entire acquisition. This allows the generation of good quality elastograms for short (sub-second) as well as long (multi-second) acquisition times. In addition, from the time-dependent behavior of the local strains or displacements occurring in the material, images of local strain time constants and local displacement time constants can be generated using curve-fitting techniques.

2. Description of the Prior Art

Prior art techniques for making time-dependent elastographic measurements require the use of a fixed pre-compression RF frame that is acquired immediately before compression and post-compression frames that are acquired sequentially at increasing time-intervals with respect to the fixed pre-compression frame. Elastograms are then generated by applying elastographic techniques between the same pre-compression frame and the successive post-compression frames. This methodology has been proven to be not adequate for imaging the temporal behavior of materials in inherently noisy environments because of the echo decorrelation problems that are encountered due to uncontrolled motion, which may be significant shortly after compression. Embodiments of the present invention overcomes the limitations of the aforementioned techniques because the elastograms are generated using frames that are sufficiently close in time to avoid decorrelation due to uncontrollable motion.

Prior art elastographic methods used to generate axial elastograms in vivo are focused on the determination of tissue's axial displacements and strains after the application of a compression. These displacements or strains are computed by using a frame that is acquired immediately before the application of the compression and a frame that is acquired immediately after the application of the compression. To minimize noise, usually the compression is divided in a multiplicity of small compression steps and at the end of each step an echo sequence is acquired. Axial displacements or strain are generated using the various echo-sequences acquired during the compression. In general, the axial displacement or strains are then averaged to reduce noise.

These prior art methods may allow obtaining axial displacement and strain of adequate quality, in vivo, but they may not allow estimating the time-dependent mechanical changes occurring in such displacements and strains in materials that exhibit mechanical properties that vary with time. Indeed the usual assumption of these prior art methods is that the target body can be modeled as a purely linearly elastic material, so that no significant time-dependent mechanical changes occur during the acquisition of the echo-sequences.

The present invention differs from the aforementioned prior art techniques because the mechanical stimulus is first applied to the target body and thereafter the echo-sequences used for determining the displacements or strains are acquired. In the present invention the time-dependent mechanical behavior of a material after the application of a mechanical stimulus is imaged by means of post-stimulus echo-sequences only. As such, the method of this invention is directed toward materials that exhibit a time dependent mechanical behavior in response to the applied mechanical stimulus. In addition, the present invention differs from the aforementioned prior art methods since embodiments of the invention are applicable not only to axial displacements and strains but also displacements and strains in all directions, displacement ratios, strain ratios and the time-dependent behavior of the aforementioned parameters can be determined and imaged.

SUMMARY OF THE INVENTION

Embodiments of this invention overcome the limitations of the current elastographic compression/acquisition methods in inherently noisy applications as for example those of clinical interest. Embodiments of this invention minimize the decorrelation noise between the frames used for the generation of the elastograms since the reference frame is continuously moved in time and the inter-frame time interval is maintained sufficiently short during the entire acquisition. This allows the generation of good quality elastograms in noisy environments for short (sub-second) as well as long (multi-second) acquisition times.

Embodiments of the invention may be practiced using the preferred hand-held configuration of scanning.

Embodiments of the invention utilize the application of a mechanical stimulus to a material that exhibits a time-dependent mechanical behavior and acquisition of ultrasonic data from the target body after the application of the mechanical stimulus. Time-dependent axial strain, lateral strain and strain ratio elastograms can be generated by using a continuously moving reference frame and post-compression frames spaced at sub-second intervals with respect to the pre-compression frame. The invention is also applicable for evaluating the time dependent changes occurring in lateral and axial displacements as well as in the slopes of these displacements and in transverse strains.

Embodiments of the invention also generate images of local strain time constants and displacement time constants that are representative of the time-dependent mechanical behavior of the material under the application of a mechanical stimulus. This is accomplished by using curve-fitting techniques to the time-dependent evolution of the local strains or local displacements and displaying the coefficients of the fitting curve as images. These images may also be of value for differentiation of materials based on the time required for the interstitial fluid to flow out of the area of interest. This may also allow the generation of new contrast mechanism, which can be helpful for detecting the presence of regions that have the same elastic properties of the surrounding background (and therefore they are not visible in the corresponding drained and undrained elastograms), but have different permeability properties.

Embodiments of the invention may allow application of the elastographic techniques for diagnosis of some pathological conditions, such as lymphedema, decubitus ulcers, and the detection of cancers and their differentiation from normal tissues via fluid transport characterization.

Several terms are used herein to describe various embodiments of the invention. The term "displacement", as used herein, refers to local time-delays estimated between two echo signals. The term "strain", as used herein, refers to the gradient of local displacements. The strain in each direction may be computed as the derivative of the displacement along that given direction.

The term "strain ratio", as used herein, refers to the ratio between the strains computed along two directions. The term "slope of the displacement", as used herein, refers to the derivative of the displacements along all possible directions.

By considering as a transverse plane any plane that is perpendicular to the transducer's beam axis and transverse displacement the displacement between any two points lying in any transverse plane, the term "transverse strain", as used herein, is the derivative of the transverse displacement.

DESCRIPTION OF THE PREFERRED EMBODIMENTS

Figure 7:
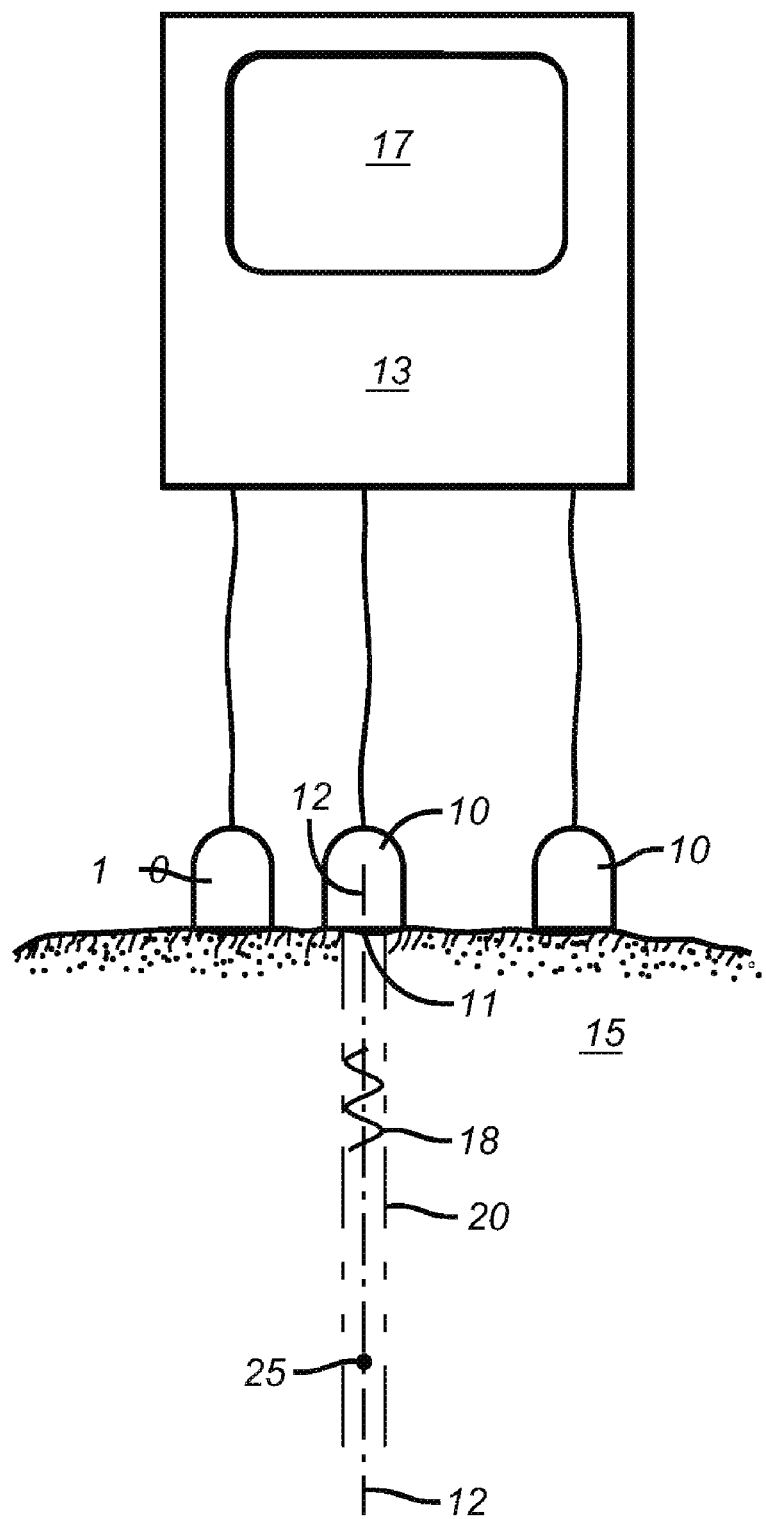
FIG. 7 is a side view of a first apparatus suitable for practicing various embodiments of the invention.

An apparatus that can be used to practice the various method embodiments of the invention is depicted in FIG. 7. FIG. 7 shows multiple transducers 10 sonically coupled to a target body 15. An ultrasonic pulse 18 is shown propagating within beam 20 toward an echo source 25 on beam axis 12. As the pulse 18 propagates through the target 15, corresponding echoes are generated and arrival items noted at the transducer aperture 11.

The transducers 10 are operatively coupled to a pulse generation and signal receiving unit 13. Unit 13 further comprises a display 17 capable of visually displaying strains, strain ratios, displacements, and slopes that are determined and/or estimated using various embodiments of the present invention, described herein. Unit 13 comprises the circuitry known to those of ordinary skill in the elastography arts to generate ultrasound pulses, receive echo signals, process echo signals, store echo signals, and display data based upon the received and processed signals.

Figure 1:
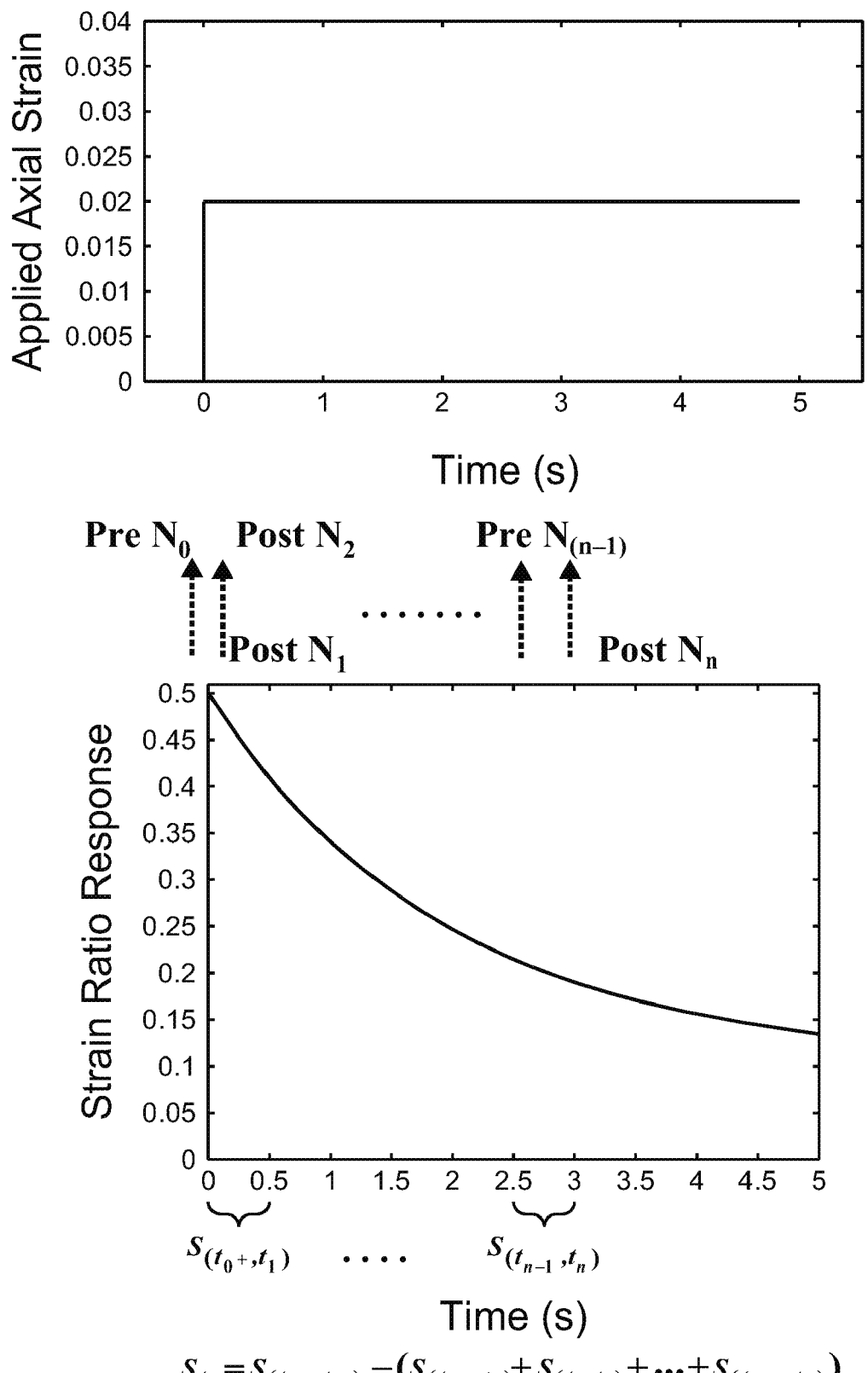
FIG. 1 provides an example of the estimation of the strain ratio from a sequence of strain ratios computed between different post compression frames.
Figure 2:
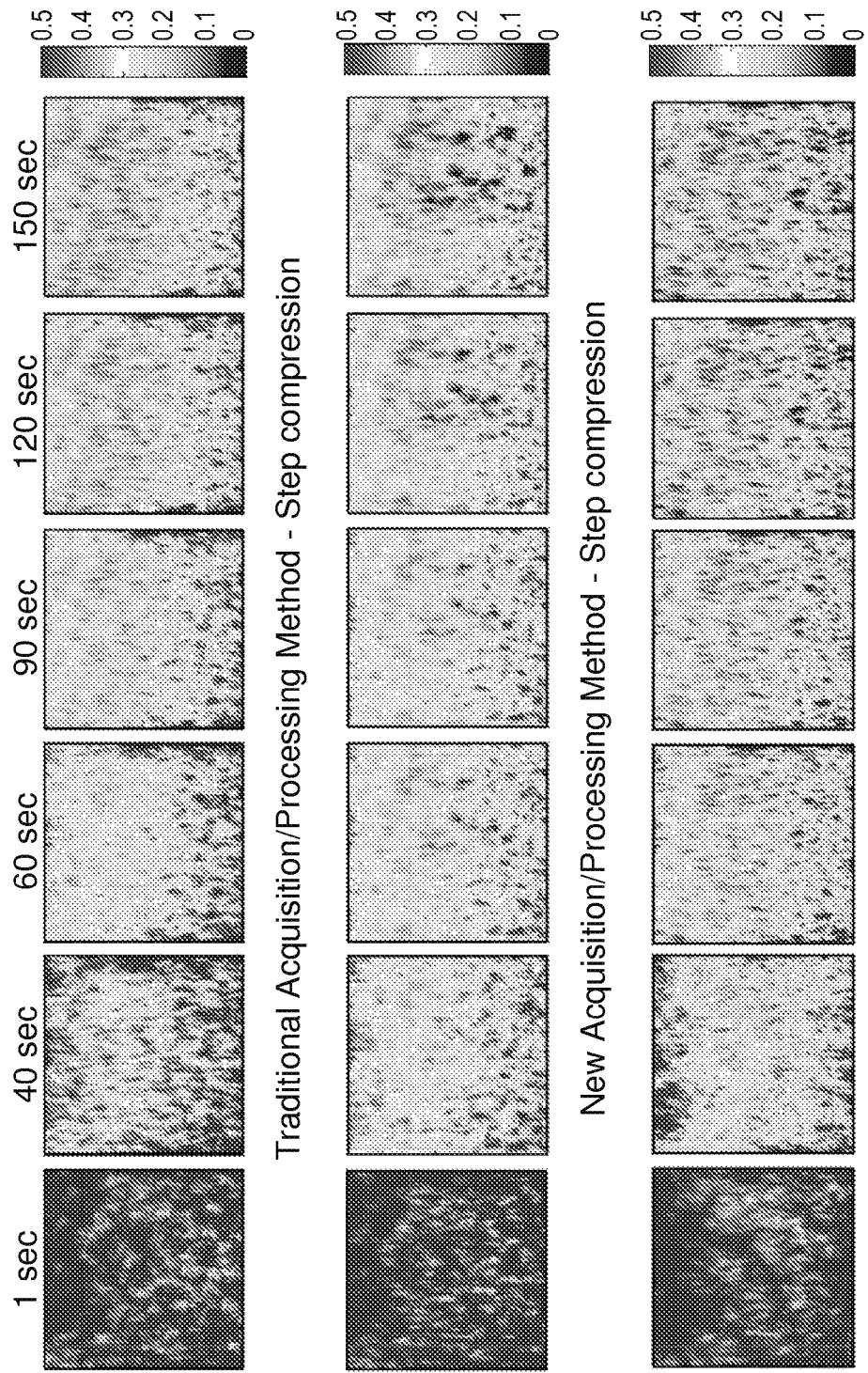
FIG. 2 provides a comparison between a poroelastogram generated using the traditional method and two elastograms obtained using the proposed method in vitro.
Figure 3A:
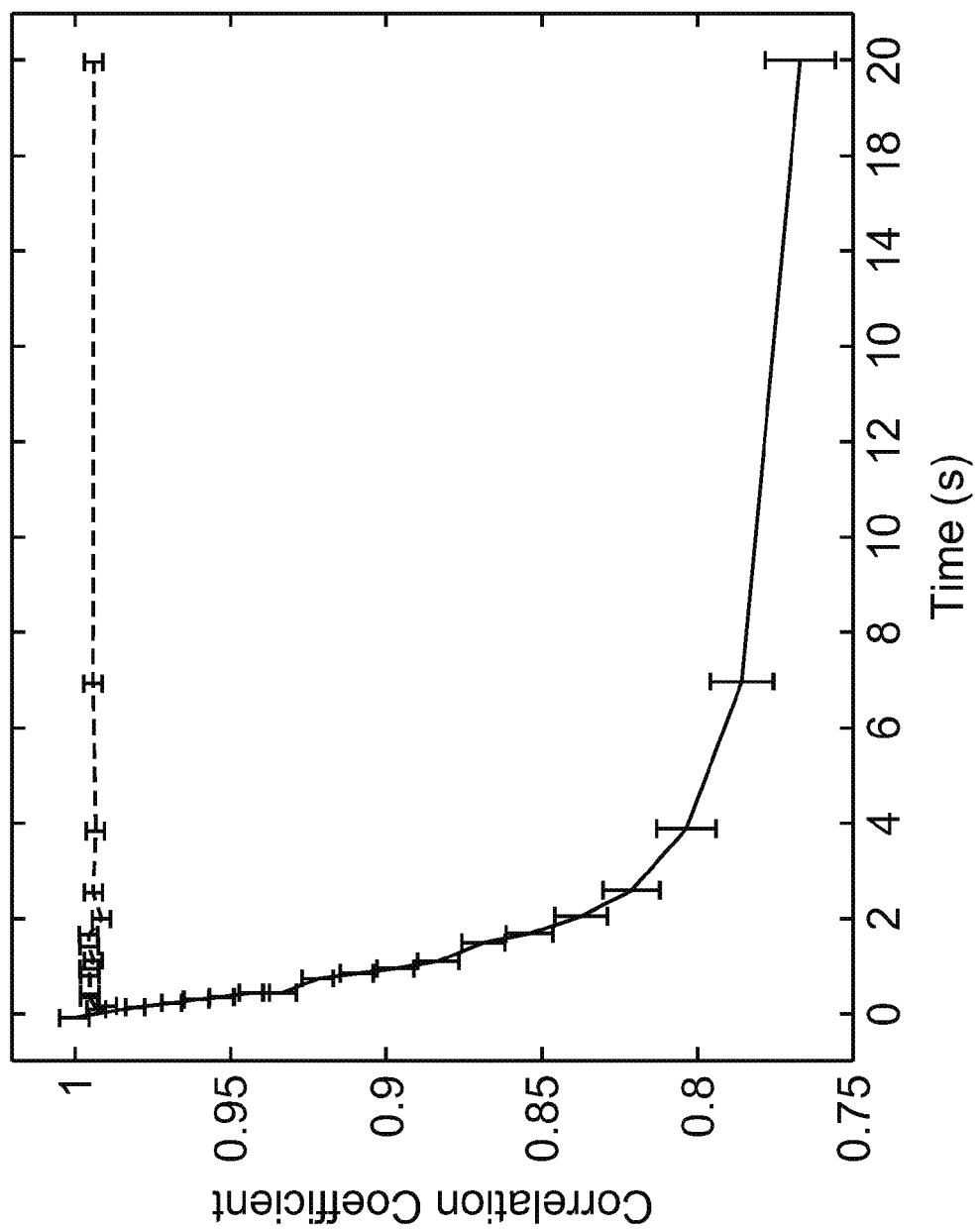
FIGS. 3A-3C provide a simulation comparison of the performances of the traditional method (solid curve) and the present invention (dashed curve) in inherently noisy applications.
Figure 3B:
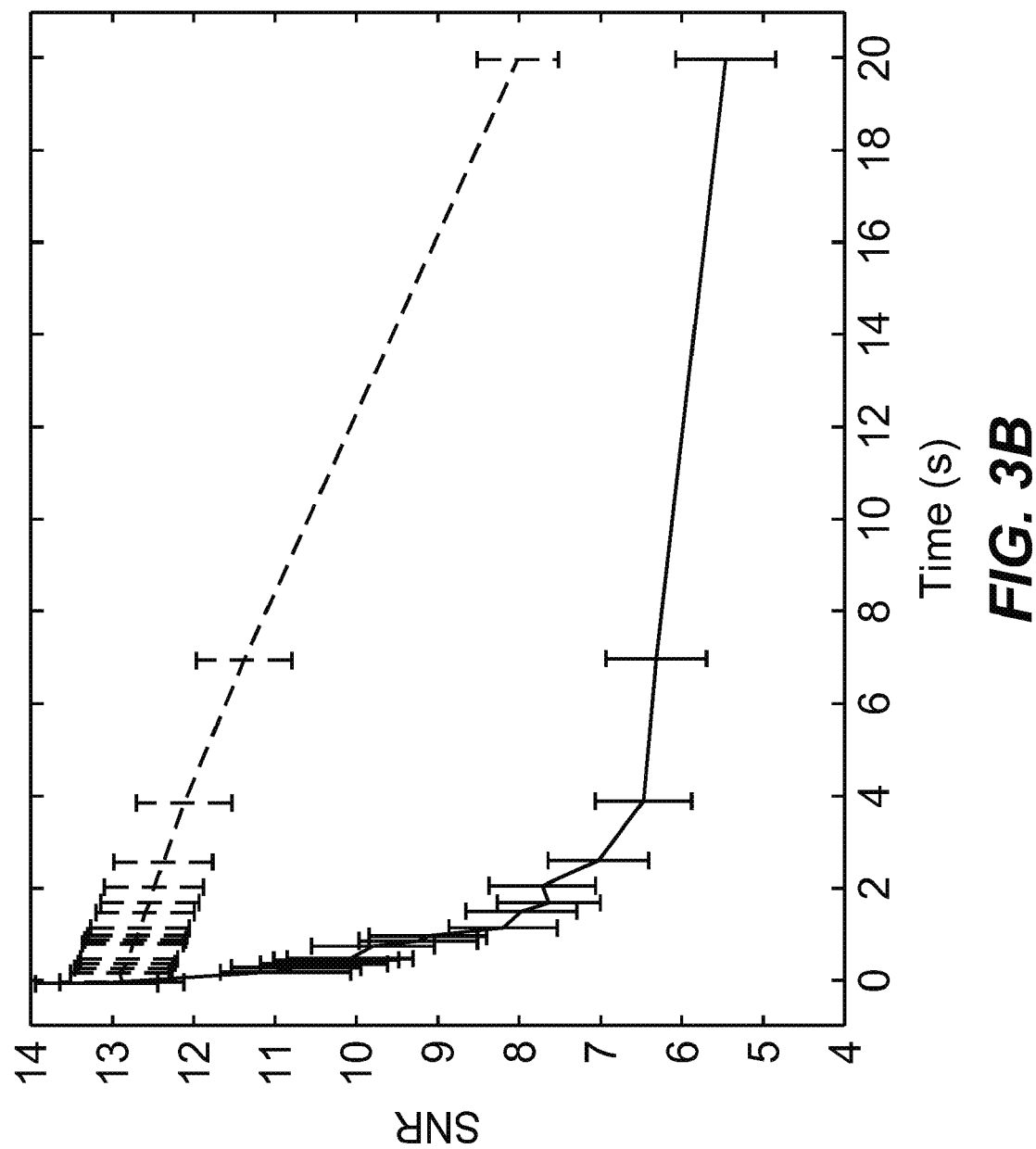
Figure 3C:
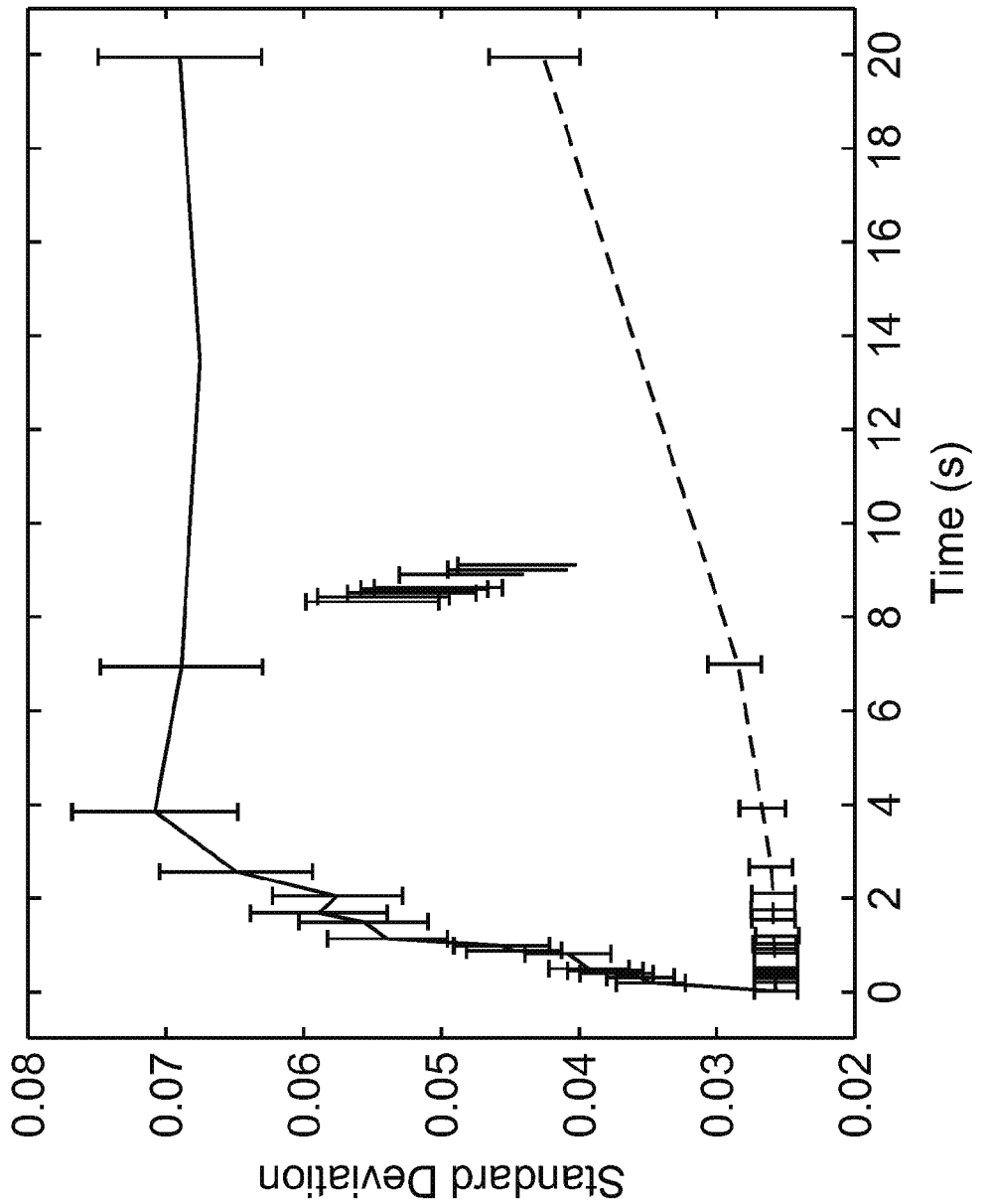
Figure 4:
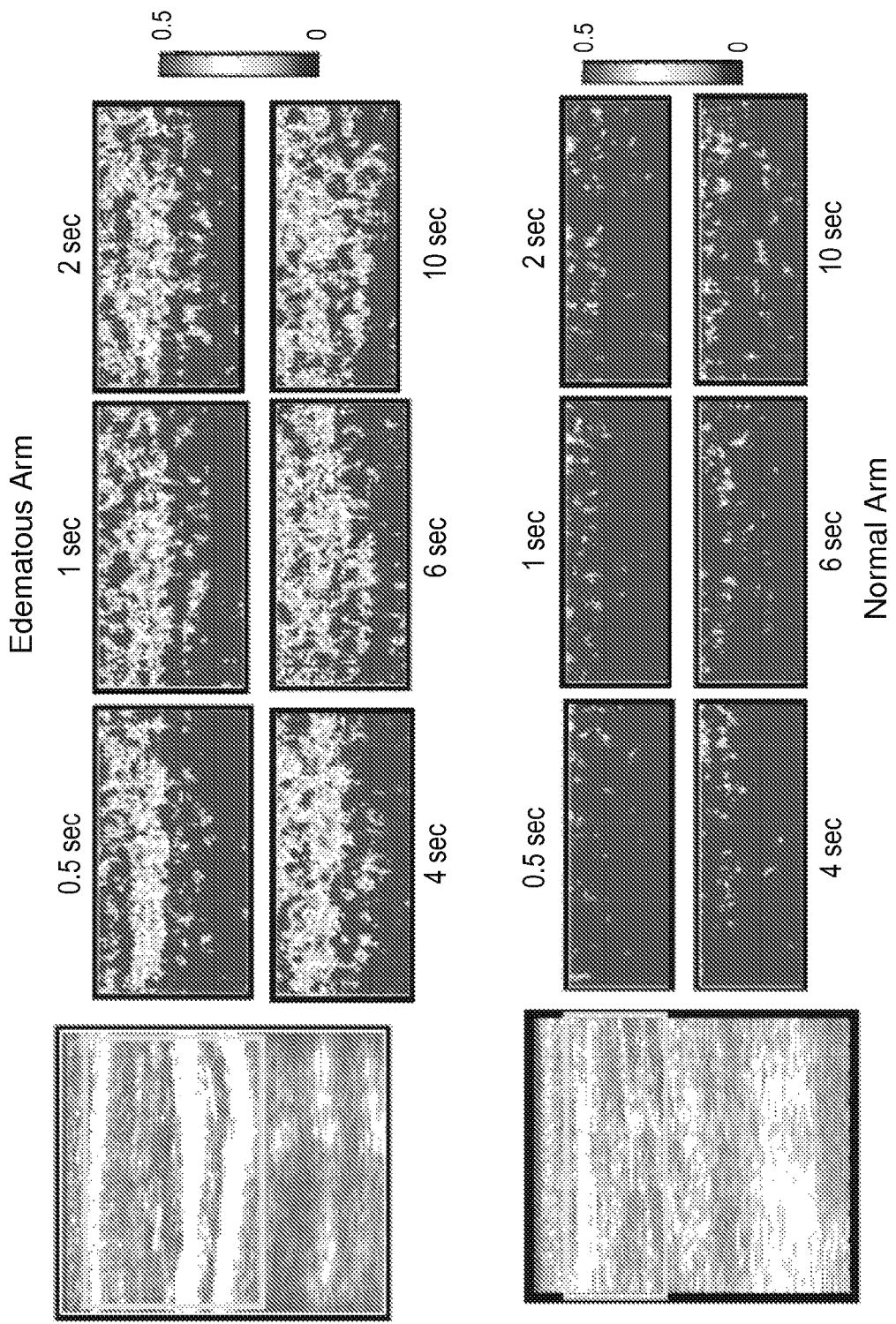
FIG. 4 is an example of the application of the new proposed method in vivo in a patient with stage 2 lymphedema in the arm. For comparison, the normal arm is shown as well.
Figure 5:
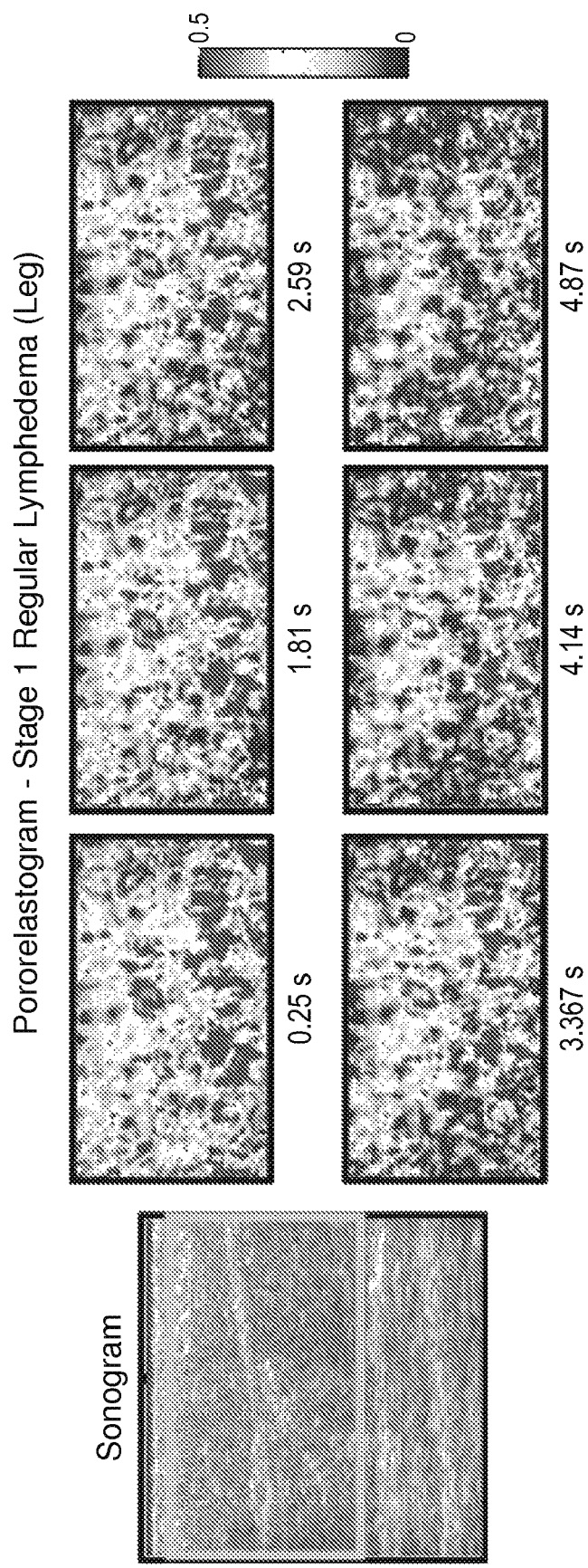
FIG. 5 is an example of the application of the new proposed method in vivo in a patient with stage 1 lymphedema in both legs.
Figure 6:
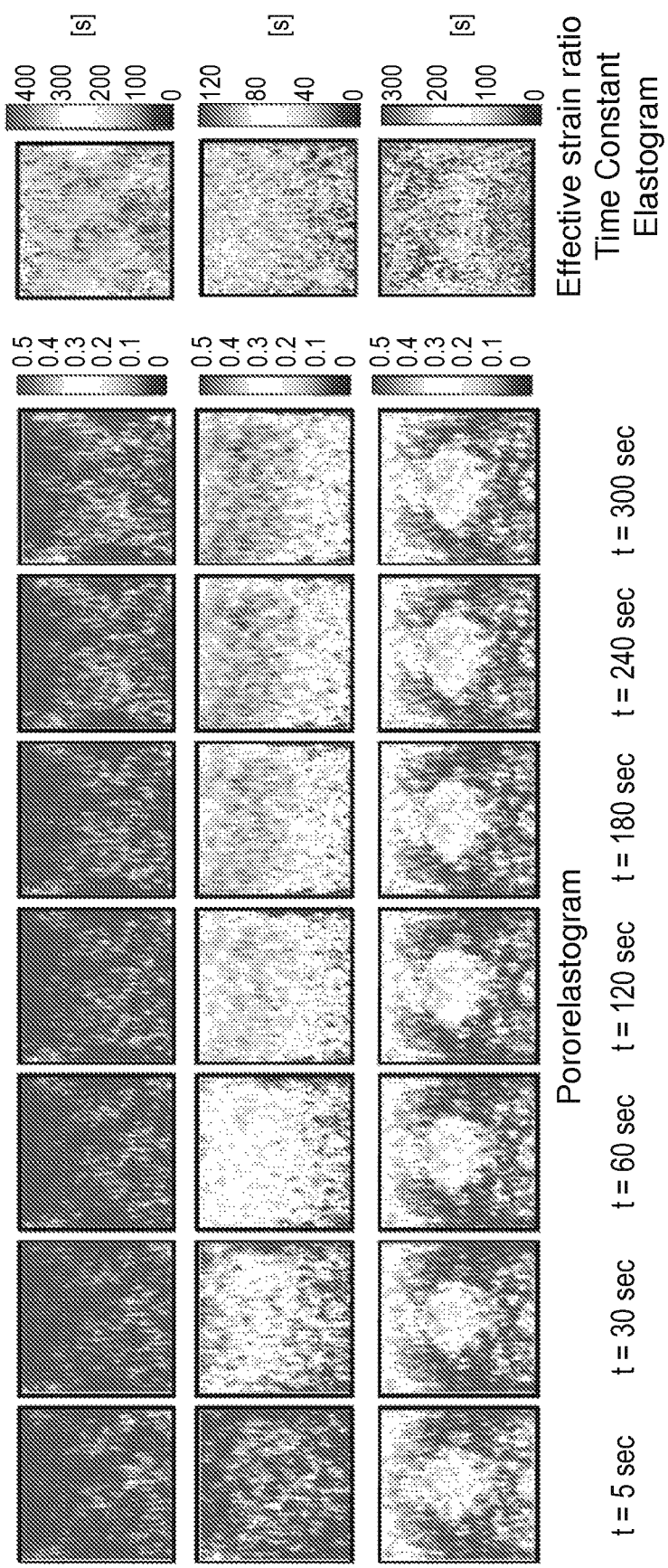
FIG. 6 shows three examples of Strain ratio time constant elastograms (right) as estimated from the corresponding poroelastograms (left) by applying curve fitting techniques.

FIGS. 3A-3C show the superior performance of the proposed method, due to the ability of this method to maintain high cross-correlation values in time. FIG. 1 provides an example of the estimation of the strain ratio from a sequence of strain ratios computed between different post compression frames. FIG. 2 provides a comparison between a poroelastogram generated using the traditional method and two elastograms obtained using the proposed method in vitro. FIG. 4 is an example of the application of the new proposed method in vivo in a patient with stage 2 lymphedema in the arm. For comparison, the normal arm is shown as well. FIG. 5 is an example of the application of the new proposed method in vivo in a patient with stage 1 lymphedema in both legs. FIG. 6 shows three examples of strain ratio time constant elastograms (right) as estimated from the corresponding poroelastograms (left) by applying curve fitting techniques.

Several embodiments of the invention are directed toward methods for determining the strain of a target body. One such embodiment comprises the step of coupling a transducer array comprising at least three transducers to the target body. In one preferred embodiment, the three transducers are positioned along a common line segment. In another preferred embodiment, one transducer is equidistantly spaced with respect to the other two transducers. In another preferred embodiment, the three transducers are positioned such that the pulses of ultrasound energy they emit travel along non-parallel paths in the target body.

The next step of this embodiment is applying a mechanical stimulus to a target body. In a preferred embodiment, the applied mechanical stimulus is selected from the group consisting of stress-relaxation, creep, constant load, constant strain, constant strain rate, constant displacement, sinusoidal load, sinusoidal strain, sinusoidal strain, increasing load, increasing strain, increasing displacement, decreasing load, decreasing strain, and decreasing displacement.

In one preferred embodiment, the applied mechanical stimulus is strain. In another preferred embodiment, the strain is applied at a constant level. In another preferred embodiment, the strain is applied at a non-constant level.

In one preferred embodiment, the mechanical stimulus is applied in the target body. In another preferred embodiment, the mechanical stimulus is applied by the target body.

In one preferred embodiment, the mechanical stimulus is generated by a change of temperature in the target body. In another preferred embodiment, the mechanical stimulus is generated by a change of temperature in the vicinity of the target body. In another preferred embodiment, the mechanical stimulus is generated by fluid flow in the target body. In another preferred embodiment, the mechanical stimulus is generated by fluid flow in the vicinity of the target body.

In one preferred embodiment, the applied mechanical stimulus is a load. In another preferred embodiment, the load is applied at a constant level. In another preferred embodiment, the load is applied at a non-constant level.

In one preferred embodiment, the applied mechanical stimulus is a displacement. In another preferred embodiment, the displacement is applied at a constant level. In another preferred embodiment, the displacement is applied at a non-constant level.

The next step of this embodiment is emitting a first pulse of ultrasound energy from each of the transducers into the target body. The next step of this embodiment is receiving with each of the transducers at least one ultrasound echo sequence from each first pulse. The next step of this embodiment is emitting a second pulse of ultrasound energy from each of the transducers into the target body. The next step of this embodiment is receiving with each of the transducers at least one ultrasound echo sequence from each second pulse. The next step of this embodiment is emitting a third pulse of ultrasound energy from each of the transducers into the target body. The next step of this embodiment is receiving with each of the transducers at least one ultrasound echo sequence from each third pulse. In a preferred embodiment, the second pulse is emitted at a first predetermined time after the first pulse and the third pulse is emitted at a second predetermined time after the second pulse.

The next step of this embodiment is estimating the strain along two directions in the target body between members of a first pair of ultrasound sequences comprising the first ultrasound echo sequence and another of the ultrasound echo sequences.

The next step of this embodiment is estimating the strain along two different directions in the target body between members of a second pair of ultrasound echo sequences comprising two ultrasound echo sequences that are not identical to the two ultrasound sequences that are comprised by the first pair. In one preferred embodiment, the two directions are orthogonal to each other. In another preferred embodiment, the two directions are orthogonal to the paths of the pulses emitted from the three transducers. In another preferred embodiment, the strain is estimated using a technique selected from the group consisting of a cross correlation technique, a Doppler technique, a phase estimator technique, a frequency estimator technique, a pattern matching technique, a sum-absolute difference technique, a least squares technique, and a zero crossing estimator technique.

In one preferred embodiment, the target body is viscoelastic. In another preferred embodiment, the target body is poroelastic. In another preferred embodiment, the target body possesses time dependent mechanical properties.

A preferred embodiment of the invention further comprises displaying the estimated strain. In another preferred embodiment, the invention comprises computing the strain ratios between the echo sequences in the first pair and between the echo sequences in the second pair. In a preferred embodiment, the invention further comprises storing the computed strain ratios in a retrievable medium.

Another embodiment of the invention for determining the strain in a target body comprises the step of applying a mechanical stimulus to a target body. The next step of this embodiment comprises coupling a transducer to the target body. The next step of this embodiment comprises emitting a first pulse of ultrasound energy from the transducer into the target body. The next step of this embodiment comprises receiving with the transducer at least one ultrasound echo sequence from the first pulse. The next step of this embodiment comprises emitting a second pulse of ultrasound energy from the transducer into the target body. The next step of this embodiment comprises receiving with the transducer at least one ultrasound echo sequence from the second pulse. The next step of this embodiment comprises emitting a third pulse of ultrasound energy from the transducer into the target body. The next step of this embodiment comprises receiving with the transducer at least one ultrasound echo sequence from the third pulse.

The next step of this embodiment comprises estimating the strain in the target body between the first ultrasound echo sequence and a subsequent ultrasound echo sequence. The next step of this embodiment comprises estimating the strain in the target body between two ultrasound echo sequences other than the two ultrasound echo sequences for which the strain was estimated in the preceding step.

In another preferred embodiment, this method further comprises displaying the estimated strain.

Another embodiment of the present invention for determining the strain of a target body comprises the step of applying a mechanical stimulus to a target body during time interval T. In one preferred embodiment, the mechanical stimulus is increasing. In another preferred embodiment, the increasing mechanical stimulus is linearly increasing. In another preferred embodiment, the mechanical stimulus is decreasing. In another preferred embodiment, the decreasing mechanical stimulus is linearly decreasing.

The next step of this embodiment comprises coupling a transducer to the target body during time interval T. The next step of this embodiment comprises emitting a first pulse of ultrasound energy from the transducer into the target body during time interval T. The next step of this embodiment comprises receiving with the transducer at least one ultrasound echo sequence from the first pulse during time interval T. The next step of this embodiment comprises emitting a second pulse of ultrasound energy from the transducer into the target body during time interval T. The next step of this embodiment comprises receiving with the transducer at least one ultrasound echo sequence from the second pulse during time interval T. The next step of this embodiment comprises emitting a third pulse of ultrasound energy from the transducer into the target body during time interval T. The next step of this embodiment comprises receiving with the transducer at least one ultrasound echo sequence from the third pulse during time interval T.

The next step of this embodiment comprises estimating the strain in the target body between the first ultrasound echo sequence and a subsequent ultrasound echo sequence. The next step of this embodiment comprises estimating the strain in the target body between two ultrasound echo sequences other than the two ultrasound echo sequences for which the strain was estimated in the preceding step.

Other embodiments of the present invention are directed toward determining the displacement of the target body. One such embodiment comprises the step of applying a mechanical stimulus to a target body. This embodiment further comprises coupling a transducer array comprising at least three transducers to the target body. This embodiment further comprises emitting a first pulse of ultrasound energy from each of the transducers into the target body. This embodiment further comprises receiving with each of the transducers at least one ultrasound echo sequence from each first pulse. This embodiment further comprises emitting a second pulse of ultrasound energy from each of the transducers into the target body. This embodiment further comprises receiving with each of the transducers at least one ultrasound echo sequence from each second pulse. This embodiment further comprises emitting a third pulse of ultrasound energy from each of the transducers into the target body. This embodiment further comprises receiving with each of the transducers at least one ultrasound echo sequence from each third pulse.

This embodiment further comprises estimating a first pair of displacements in two directions in the target body between a first pair of ultrasound sequences comprising the first ultrasound echo sequence and another of said ultrasound echo sequence. This embodiment further comprises estimating a second pair of displacements in two directions in the target body between a second pair of ultrasound echo sequences comprising two ultrasound echo sequences that are not identical to the two ultrasound sequences that are comprised by said first pair. In a preferred embodiment, this method further comprises displaying the estimated displacements.

In another preferred embodiment, this method further comprises estimating the slopes of the first pair of displacements in any direction to estimate the first pair of strains in the target body in two directions. This preferred embodiment further comprises estimating the slopes of the second pair of displacements in any direction to estimate the second pair of strains in the target body in two directions. In another preferred embodiment, this method further comprises computing the first strain ratio between the first pair of strains and computing the second strain ratio between the second pair of strains. In another preferred embodiment, this method further comprises adding the first and second strain ratios. In another preferred embodiment, this method further comprises determining the difference between the first strain ratio and the second strain ratio. This method may be practiced by subtracting the first strain ratio from the second strain ratio, or by subtracting the second strain ratio from the first strain ratio.

In another preferred embodiment, this method further comprises estimating the slopes of the first pair of displacements in any direction to estimate the transverse strains in the target body, and estimating the slope of the second pair of displacements in any direction to estimate the transverse strains in the target body.

Another embodiment to of the present invention directed to determining the displacement of a target body comprises the step of applying a mechanical stimulus to a target body. The next step in this embodiment comprises coupling a transducer to the target body. The next step in this embodiment comprises emitting a first pulse of ultrasound energy from the transducer into the target body. The next step in this embodiment comprises receiving with the transducer at least one ultrasound echo sequence from the first pulse. The next step in this embodiment comprises emitting a second pulse of ultrasound energy from the transducer into the target body. The next step in this embodiment comprises receiving with the transducer at least one ultrasound echo sequence from the second pulse. The next step in this embodiment comprises emitting a third pulse of ultrasound energy from the transducer into the target body. The next step in this embodiment comprises receiving with the transducer at least one ultrasound echo sequence from the third pulse.

The next step in this embodiment comprises estimating the first displacement in the target body between the first ultrasound echo sequence and a subsequent ultrasound echo sequence. The next step in this embodiment comprises estimating the second displacement in the target body between two ultrasound echo sequences other than the two ultrasound echo sequences for which the displacement was estimated in the preceding step. In another preferred embodiment, this method further comprises displaying the estimated first and second displacements.

In a preferred embodiment, this method further comprises estimating the slope of the first displacement in any direction to estimate the first strain in the target body and estimating the slope of the second displacement in any direction to estimate the second strain in the target body. In another preferred embodiment, this method further comprises estimating the slope of the first displacement in any direction to estimate the first transverse strain in the target body and estimating the slope of second displacement in any direction to estimate the second transverse strain in the target body. In another preferred embodiment, this method further comprises computing the strains from the estimated first and second displacements. In another preferred embodiment, the invention further comprises displaying the computed strains. In another preferred embodiment, the invention further comprises computing the sum of the first and second displacements and estimating the strain from some of the displacements previously computed. In a preferred embodiment, the sum of the first and second displacements can be computed by adding the magnitudes of the first and second displacements. In another preferred embodiment, the invention further comprises displaying the sum of the first and second displacements. In a preferred embodiment, this invention further comprises displaying the estimated strain.

In a preferred embodiment, this method further comprises determining the difference between the first and second displacements and estimating the strain from the computed difference between the first and second displacements. In a preferred embodiment, the difference between the first and second displacements may be determined by subtracting the first displacement from the second displacement or by subtracting the second displacement from the first displacement. In another preferred embodiment, the invention further comprises displaying the difference between the first and second displacements. In another preferred embodiment, the invention further comprises displaying the difference between the first and second displacements. In another preferred embodiment, the invention further comprises displaying the estimated strain. In another preferred embodiment, the invention further comprises determining the sum of the first and second displacements and estimating the slope of the sum of the first and second displacements in any direction to estimate transverse strains. In a preferred embodiment, the invention further comprises determining the difference between the first and second displacements and estimating the slope of the difference between the first and second displacements in any direction to estimate transverse strain.

Another embodiment to the present invention directed toward determining the displacement of a target body comprises applying a mechanical stimulus to a target body during time interval T. This embodiment further comprises coupling a transducer to the target body during time interval T. This embodiment further comprises emitting a first pulse of ultrasound energy from the transducer into the target body during time interval T. This embodiment further comprises receiving with the transducer at least one ultrasound echo sequence from the first pulse during time interval T. This embodiment further comprises emitting a second pulse of ultrasound energy from the transducer into the target body during time interval T. This embodiment further comprises receiving with the transducer at least one ultrasound echo sequence from the second pulse during time interval T. This embodiment further comprises emitting a third pulse of ultrasound energy from the transducer into the target body during time interval T. This embodiment further comprises receiving with the transducer at least one ultrasound echo sequence from the third pulse during time interval T.

This embodiment further comprises estimating the first displacement in the target body in between the first ultrasound echo sequence and a subsequent ultrasound echo sequence. This embodiment further comprises estimating the second displacement in the target body between two ultrasound echo sequences other than the two ultrasound echo sequences for which the displacement was estimated in the preceding step. In a preferred embodiment, the invention further comprises displaying the estimated displacement. In another preferred embodiment, the invention further comprises computing the strain from the first displacement and computing the strain from the second displacement. In another preferred embodiment, the invention further comprises computing the transverse strain from the first displacement and computing the transverse strain from the second displacement.

Another embodiment to the present invention directed toward determining the displacement of a target body comprises applying a mechanical stimulus to a target body. This embodiment further comprises coupling a transducer array comprising at least three transducers to the target body. This embodiment further comprises emitting a first pulse of ultrasound energy from each of the transducers into the target body. This embodiment further comprises receiving with each of the transducers at least one ultrasound echo sequence from each first pulse. This embodiment further comprises emitting a second pulse of ultrasound energy from each of the transducers into the target body. This embodiment further comprises receiving with each of the transducers at least one ultrasound echo sequence from each second pulse. This embodiment further comprises emitting a third pulse of ultrasound energy from each of the transducers into the target body. This embodiment further comprises receiving with each of the transducers at least one ultrasound echo sequence from each third pulse. This embodiment further comprises estimating the strain in two directions in the target body between a first pair of ultrasound sequences comprising the first ultrasound echo sequence and another of said ultrasound echo sequences. This embodiment further comprises estimating the strain in two directions in the target body between a second pair of ultrasound echo sequences comprising two ultrasound echo sequences that are not identical to the two ultrasound sequences that are comprised by said first pair.

Another embodiment to the present invention directed toward determining the displacement of a target body comprises coupling a transducer to the target body. This embodiment further comprises applying a mechanical stimulus to a target body. This embodiment further comprises emitting a first pulse of ultrasound energy from the transducer into the target body. This embodiment further comprises receiving with the transducers at least one ultrasound echo sequence from the first pulse. This embodiment further comprises emitting a second pulse of ultrasound energy from the transducer into the target body. This embodiment further comprises receiving with the transducer at least one ultrasound echo sequence from the second pulse. This embodiment further comprises emitting a third pulse of ultrasound energy from the transducer into the target body. This embodiment further comprises receiving with the transducer at least one ultrasound echo sequence from the third pulse. This embodiment further comprises estimating the strain in the target body between the first ultrasound echo sequence and a subsequent ultrasound echo sequence. This embodiment further comprises estimating the strain in the target body between two ultrasound echo sequences other than the two ultrasound echo sequences for which the strain was estimated in the preceding step.

Another embodiment to the present invention directed toward determining the displacement of a target body comprises coupling a transducer to the target. This embodiment further comprises applying a mechanical stimulus to a target body during time interval T. This embodiment further comprises emitting a first pulse of ultrasound energy from the transducer into the target body during time interval T. This embodiment further comprises receiving with the transducer at least one ultrasound echo sequence from the first pulse during time interval T. This embodiment further comprises emitting a second pulse of ultrasound energy from the transducer into the target body during time interval T. This embodiment further comprises receiving with the transducer at least one ultrasound echo sequence from the second pulse during time interval T. This embodiment further comprises emitting a third pulse of ultrasound energy from the transducer into the target body during time interval T. This embodiment further comprises receiving with the transducer at least one ultrasound echo sequence from the third pulse during time interval T. This embodiment further comprises estimating the strain in the target body in between the first ultrasound echo sequence and a subsequent ultrasound echo sequence. This embodiment further comprises estimating the strain in the target body between two ultrasound echo sequences other than the two ultrasound echo sequences for which the strain was estimated in the preceding step.

Another embodiment to the present invention directed toward determining the displacement of a target body comprises coupling a transducer array comprising at least three transducers to the target body. This embodiment further comprises applying a mechanical stimulus to a target body. This embodiment further comprises emitting a first pulse of ultrasound energy from each of the transducers into the target body. This embodiment further comprises receiving with the transducer at least one ultrasound echo sequence from each first pulse. This embodiment further comprises emitting a second pulse of ultrasound energy from each of the transducers into the target body. This embodiment further comprises receiving with the transducer at least one ultrasound echo sequence from each second pulse. This embodiment further comprises emitting a third pulse of ultrasound energy from each of the transducers into the target body. This embodiment further comprises receiving with the transducer at least one ultrasound echo sequence from each third pulse. This embodiment further comprises estimating the first pair of displacement in two directions in the target body between a first pair of ultrasound sequences comprising the first ultrasound echo sequence and another of said ultrasound echo sequences. This embodiment further comprises estimating the second pair of displacement in two directions in the target body between a second pair of ultrasound echo sequences comprising two ultrasound echo sequences that are not identical to the two ultrasound sequences that are comprised by said first pair.

Another embodiment to the present invention directed toward determining the displacement of a target body comprises coupling a transducer to the target body. This embodiment further comprises applying a mechanical stimulus to a target body. This embodiment further comprises emitting a first pulse of ultrasound energy from the transducer into the target body. This embodiment further comprises receiving with the transducer at least one ultrasound echo sequence from the first pulse. This embodiment further comprises emitting a second pulse of ultrasound energy from the transducer into the target body. This embodiment further comprises receiving with the transducer at least one ultrasound echo sequence from the second pulse. This embodiment further comprises emitting a third pulse of ultrasound energy from the transducer into the target body. This embodiment further comprises receiving with the transducer at least one ultrasound echo sequence from the third pulse. This embodiment further comprises estimating the displacement in the target body between the first ultrasound echo sequence and a subsequent ultrasound echo sequence. This embodiment further comprises estimating the displacement in the target body between two ultrasound echo sequences other than the two ultrasound echo sequences for which the strain was estimated in the preceding step.

Another embodiment to the present invention directed toward determining the displacement of a target body comprises coupling a transducer to the target body. This embodiment further comprises applying a mechanical stimulus to a target body during time interval T. This embodiment further comprises emitting a first pulse of ultrasound energy from the transducer into the target body during time interval T. This embodiment further comprises receiving with the transducer at least one ultrasound echo sequence from the first pulse during time interval T. This embodiment further comprises emitting a second pulse of ultrasound energy from the transducer into the target body during time interval T. This embodiment further comprises receiving with the transducer at least one ultrasound echo sequence from the second pulse during time interval T. This embodiment further comprises emitting a third pulse of ultrasound energy from the transducer into the target body during time interval T. This embodiment further comprises receiving with the transducer at least one ultrasound echo sequence from the third pulse during time interval T. This embodiment further comprises estimating the displacement in the target body in between the first ultrasound echo sequence and a subsequent ultrasound echo sequence. This embodiment further comprises estimating the displacement in the target body between two ultrasound echo sequences other than the two ultrasound echo sequences for which the strain was estimated in the preceding step.

An embodiment of the invention for imaging the strain in a target body comprises applying a mechanical stimulus to a target body, wherein said application commences at a time T0. This embodiment further comprises coupling a transducer to the target body. This embodiment further comprises emitting a first pulse of ultrasound energy from the transducer into the target body. This embodiment further comprises receiving with the transducer at least one ultrasound echo sequence from the first pulse at time interval T1 after T0. This embodiment further comprises emitting a second pulse of ultrasound energy from the transducer into the target body. This embodiment further comprises receiving with the transducer at least one ultrasound echo sequence from the second pulse at time interval T2 after T0. This embodiment further comprises emitting a third pulse of ultrasound energy from the transducer into the target body. This embodiment further comprises receiving with the transducer at least one ultrasound echo sequence from the third pulse at time interval T3 after T0. This embodiment further comprises emitting a fourth pulse of ultrasound energy from the transducer into the target body. This embodiment further comprises receiving with the transducer at least one ultrasound echo sequence from the fourth pulse at time interval T4 after T0. This embodiment further comprises estimating the strain ratio, SR1, between the first ultrasound echo sequence and the second ultrasound sequence. This embodiment further comprises estimating the strain ratio, SR2, between the second ultrasound echo sequence and the third ultrasound sequence. This embodiment further comprises estimating the strain ratio, SR3, between the third ultrasound echo sequence and the fourth ultrasound sequence. This embodiment further comprises deriving a polynomial comprising at least one coefficient defining a functional relationship between time and SR1, SR2, and SR3. This embodiment further comprises imaging the coefficients of the polynomial derived in the preceding step.

An embodiment of the invention for imaging the strain in a target body comprises coupling a transducer to the target body. This embodiment further comprises applying a mechanical stimulus to a target body, wherein said application commences at a time T0. This embodiment further comprises emitting a first pulse of ultrasound energy from the transducer into the target body. This embodiment further comprises receiving with the transducer at least one ultrasound echo sequence from the first pulse at time interval T1 after T0. This embodiment further comprises emitting a second pulse of ultrasound energy from the transducer into the target body. This embodiment further comprises receiving with the transducer at least one ultrasound echo sequence from the second pulse at time interval T2 after T0. This embodiment further comprises emitting a third pulse of ultrasound energy from the transducer into the target body. This embodiment further comprises receiving with the transducer at least one ultrasound echo sequence from the third pulse at time interval T3 after T0. This embodiment further comprises emitting a fourth pulse of ultrasound energy from the transducer into the target body. This embodiment further comprises receiving with the transducer at least one ultrasound echo sequence from the fourth pulse at time interval T4 after T0. This embodiment further comprises estimating the strain, S1, between the first ultrasound echo sequence and the second ultrasound sequence. This embodiment further comprises estimating the strain, S2, between the second ultrasound echo sequence and the third ultrasound sequence. This embodiment further comprises estimating the strain, S3, between the third ultrasound echo sequence and the fourth ultrasound sequence. This embodiment further comprises deriving a polynomial comprising at least one coefficient defining a functional relationship between time and S1, S2, and S3. This embodiment further comprises imaging the coefficients of the polynomial derived in the preceding step.

An embodiment of the invention for imaging the displacement in a target body comprises coupling a transducer to the target body. This embodiment further comprises applying a mechanical stimulus to a target body, wherein said application commences at a time T0. This embodiment further comprises emitting a first pulse of ultrasound energy from the transducer into the target body. This embodiment further comprises receiving with the transducer at least one ultrasound echo sequence from the first pulse at time interval T1 after T0. This embodiment further comprises emitting a second pulse of ultrasound energy from the transducer into the target body. This embodiment further comprises receiving with the transducer at least one ultrasound echo sequence from the second pulse at time interval T2 after T0. This embodiment further comprises emitting a third pulse of ultrasound energy from the transducer into the target body. This embodiment further comprises receiving with the transducer at least one ultrasound echo sequence from the third pulse at time interval T3 after T0. This embodiment further comprises emitting a fourth pulse of ultrasound energy from the transducer into the target body. This embodiment further comprises receiving with the transducer at least one ultrasound echo sequence from the fourth pulse at time interval T4 after T0. This embodiment further comprises estimating the displacement, D1, between the first ultrasound echo sequence and the second ultrasound sequence. This embodiment further comprises estimating the displacement, D2, between the second ultrasound echo sequence and the third ultrasound sequence. This embodiment further comprises estimating the displacement, D3, between the third ultrasound echo sequence and the fourth ultrasound sequence. This embodiment further comprises deriving a polynomial comprising at least 1 coefficient defining a functional relationship between time and D1, D2, and D3. This embodiment further comprises imaging the coefficients of the polynomial derived in the preceding step.

An embodiment to the present invention directed toward measuring the mechanical stimulus applied to a target body during hand-held scanning, comprises coupling a transducer to the target body. This embodiment further comprises emitting a first pulse of ultrasound energy from the transducer into the target body. This embodiment further comprises receiving with the transducer at least one ultrasound echo sequence from the first pulse. This embodiment further comprises estimating the first distance between the transducer and a non-moving reference point in the vicinity of the target body from the first received echo sequence. This embodiment further comprises emitting a second pulse of ultrasound energy from the transducer into the target body.

This embodiment further comprises receiving with the transducer at least one ultrasound echo sequence from the second pulse. This embodiment further comprises estimating the second distance between the transducer and the same non-moving reference point used in step (d) from the second received echo sequence. In a preferred embodiment, this method further comprises computing the displacement between the first distance and the second distance.

Another embodiment to the present invention directed toward measuring the mechanical stimulus applied to a target body during hand-held scanning comprises coupling a transducer to the target body. This embodiment further comprises emitting a first pulse of ultrasound energy from the transducer into the target body. This embodiment further comprises receiving with the transducer at least one ultrasound echo sequence from the first pulse. This embodiment further comprises estimating the distance between a reference point in the vicinity of the transducer and a non-moving reference point in the vicinity of the target body from the first received echo sequence. This embodiment further comprises emitting a second pulse of ultrasound energy from the transducer into the target body. This embodiment further comprises receiving with the transducer at least one ultrasound echo sequence from the second pulse. This embodiment further comprises estimating the distance between the reference point in the vicinity of the transducer used in step (d) and the same non-moving reference point used in step (d) from the second received echo sequence.

It will be understood that various changes in detail, parameters, and arrangements of the steps which have been described and illustrated above in order to explain the nature of this invention may be made by those skilled in the art without departing from the principle and scope of the invention.

What is claimed is:

1. A method for determining the displacement of a target body, comprising:
   a. applying a mechanical stimulus to a target body;
   b. coupling a transducer array comprising at least three transducers to the target body;
   c. emitting a first pulse of ultrasound energy from each of the transducers into the target body;
   d. receiving with each of the transducers at least one ultrasound echo sequence from each first pulse;
   e. emitting a second pulse of ultrasound energy from each of the transducers into the target body;
   f. receiving with each of the transducers at least one ultrasound echo sequence from each second pulse;
   g. emitting a third pulse of ultrasound energy from each of the transducers into the target body;
   h. receiving with each of the transducers at least one ultrasound echo sequence from each third pulse;
   i. estimating a first pair of displacements in two directions in the target body between a first pair of ultrasound sequences comprising the first ultrasound echo sequence and another of said ultrasound echo sequence; and
   j. estimating a second pair of displacements in two directions in the target body between a second pair of ultrasound echo sequences comprising two ultrasound echo sequences that are not identical to the two ultrasound sequences that are comprised by said first pair.

2. The method of claim 1, further comprising displaying the estimated displacements.

3. The method of claim 1, further comprising:
   k. estimating the slopes of the first pair of displacements computed in steps (i) in any direction to estimate a first pair of strains in the target body in two directions; and
   l. estimating the slopes of the second pair of displacements computed in steps (j) in any direction to estimate a second pair of strains in the target body in two directions.

4. The method of claim 3, further comprising:
   m. computing the first strain ratio between the first pair of strains computed in step (k); and
   n. computing the second strain ratio between the second pair of strains computed in step (l).

5. The method of claim 4, further comprising adding the first and second strain ratios computed in steps (m) and (n).

6. The method of claim 4, further comprising determining the difference between the first strain ratio computed in step (m) and the second strain ratio computed in step (n).

7. The method of claim 1, further comprising:
   o. estimating the slopes of the first pair of displacements computed in step (i) in any direction to estimate transverse strains in the target body; and
   p. estimating the slopes of the second pair of displacements computed in step (j) in any direction to estimate transverse strains in the target body.

8. A method for determining the displacement of a target body, comprising:
   a. applying a mechanical stimulus to a target body;
   b. coupling a transducer to the target body;
   c. emitting a first pulse of ultrasound energy from the transducer into the target body;
   d. receiving with the transducer at least one ultrasound echo sequence from the first pulse;
   e. emitting a second pulse of ultrasound energy from the transducer into the target body;
   f. receiving with the transducer at least one ultrasound echo sequence from the second pulse;
   g. emitting a third pulse of ultrasound energy from the transducer into the target body;
   h. receiving with the transducer at least one ultrasound echo sequence from the third pulse;
   i. estimating the first displacement in the target body between the first ultrasound echo sequence and a subsequent ultrasound echo sequence; and
   j. estimating the second displacement in the target body between two ultrasound echo sequences other than the two ultrasound echo sequences for which the displacement was estimated in the preceding step.

9. The method of claim 8, further comprising displaying the estimated first and second displacements.

10. The method of claim 8, further comprising:
k. estimating the slope of the first displacement computed in step (i) in any direction to estimate a first strain in the target body; and
l. estimating the slope of the second displacement computed in step (j) in any direction to estimate a second strain in the target body.

11. The method of claim 8, further comprising:
m. estimating the slope of the first displacement computed in step (i) in any direction to estimate a first transverse strain in the target body; and
n. estimating the slope of the second displacement computed in step (j) in any direction to estimate a second transverse strain in the target body.

12. The method of claim 8, further comprising computing strains from the estimated first and second displacements.

13. The method of claim 12, further comprising displaying the computed strains.

14. The method of claim 8, further comprising:
o. computing the sum of the first and second displacements; and
p. estimating strain from the sum of the displacements computed in the preceding step.

15. The method of claim 14, further comprising displaying the sum of the first and second displacements.

16. The method of claim 14, further comprising displaying the estimated strain.

17. The method of claim 8, further comprising:
q. determining the difference between the first and second displacements; and
r. estimating strain from the difference computed in the preceding step.

18. The method of claim 17, further comprising displaying the difference between the first and second displacements.

19. The method of claim 17, further comprising displaying the estimated strain.

20. The method of claim 8, further comprising:
s. determining the sum of the first and second displacements; and
t. estimating the slope of the sum of the first and second displacements in any direction to estimate transverse strain.

21. The method of claim 8, further comprising:
u. determining the difference between the first and second displacements; and
v. estimating the slope of the difference between the first and second displacements step in any direction to estimate transverse strain.

22. A method for determining the displacement of a target body, comprising:
a. applying a mechanical stimulus to a target body during time interval T;
b. coupling a transducer to the target body during time interval T;
c. emitting a first pulse of ultrasound energy from the transducer into the target body during time interval T;
d. receiving with the transducer at least one ultrasound echo sequence from the first pulse during time interval T;
e. emitting a second pulse of ultrasound energy from the transducer into the target body during time interval T;
f. receiving with the transducer at least one ultrasound echo sequence from the second pulse during time interval T;
g. emitting a third pulse of ultrasound energy from the transducer into the target body during time interval T;
h. receiving with the transducer at least one ultrasound echo sequence from the third pulse during time interval T;
i. estimating the first displacement in the target body in between the first ultrasound echo sequence and a subsequent ultrasound echo sequence; and
j. estimating the second displacement in the target body between two ultrasound echo sequences other than the two ultrasound echo sequences for which the displacement was estimated in the preceding step.

23. The method of claim 22, further comprising displaying the estimated displacement.

24. The method of claim 22, further comprising:
k. computing strain from the first displacement; and
l. computing strain from the second displacement.

25. The method of claim 22, further comprising:
m. computing transverse strain from the first displacement; and
n. computing transverse strain from the second displacement.

26. A method for determining the displacement of a target body, comprising:
a. coupling a transducer array comprising at least three transducers to the target body;
b. applying a mechanical stimulus to a target body;
c. emitting a first pulse of ultrasound energy from each of the transducers into the target body;
d. receiving with each of the transducers at least one ultrasound echo sequence from each first pulse;
e. emitting a second pulse of ultrasound energy from each of the transducers into the target body;
f. receiving with each of the transducers at least one ultrasound echo sequence from each second pulse;
g. emitting a third pulse of ultrasound energy from each of the transducers into the target body;
h. receiving with each of the transducers at least one ultrasound echo sequence from each third pulse;
i. estimating a first pair of displacements in two directions in the target body between a first pair of ultrasound sequences comprising the first ultrasound echo sequence and another of said ultrasound echo sequences; and
j. estimating a second pair of displacements in two directions in the target body between a second pair of ultrasound echo sequences comprising two ultrasound echo sequences that are not identical to the two ultrasound sequences that are comprised by said first pair.

27. A method for determining the displacement of a target body, comprising:
a. coupling a transducer to the target body;
b. applying a mechanical stimulus to a target body;
c. emitting a first pulse of ultrasound energy from the transducer into the target body;
d. receiving with the transducer at least one ultrasound echo sequence from the first pulse;
e. emitting a second pulse of ultrasound energy from the transducer into the target body;
f. receiving with the transducer at least one ultrasound echo sequence from the second pulse;
g. emitting a third pulse of ultrasound energy from the transducer into the target body;
h. receiving with the transducer at least one ultrasound echo sequence from the third pulse;
i. estimating the displacement in the target body between the first ultrasound echo sequence and a subsequent ultrasound echo sequence; and
j. estimating the displacement in the target body between two ultrasound echo sequences other than the two ultrasound echo sequences for which the displacement was estimated in the preceding step.

28. A method for determining the displacement of a target body, comprising:
- a. coupling a transducer to the target body;
- b. applying a mechanical stimulus to a target body during time interval T;
- c. emitting a first pulse of ultrasound energy from the transducer into the target body during time interval T;
- d. receiving with the transducer at least one ultrasound echo sequence from the first pulse during time interval T;
- e. emitting a second pulse of ultrasound energy from the transducer into the target body during time interval T;
- f. receiving with the transducer at least one ultrasound echo sequence from the second pulse during time interval T;
- g. emitting a third pulse of ultrasound energy from the transducer into the target body during time interval T;
- h. receiving with the transducer at least one ultrasound echo sequence from the third pulse during time interval T;
- i. estimating the displacement in the target body in between the first ultrasound echo sequence and a subsequent ultrasound echo sequence; and
- j. estimating the displacement in the target body between two ultrasound echo sequences other than the two ultrasound echo sequences for which the displacement was estimated in the preceding step.

* * * * *